Figure 1:
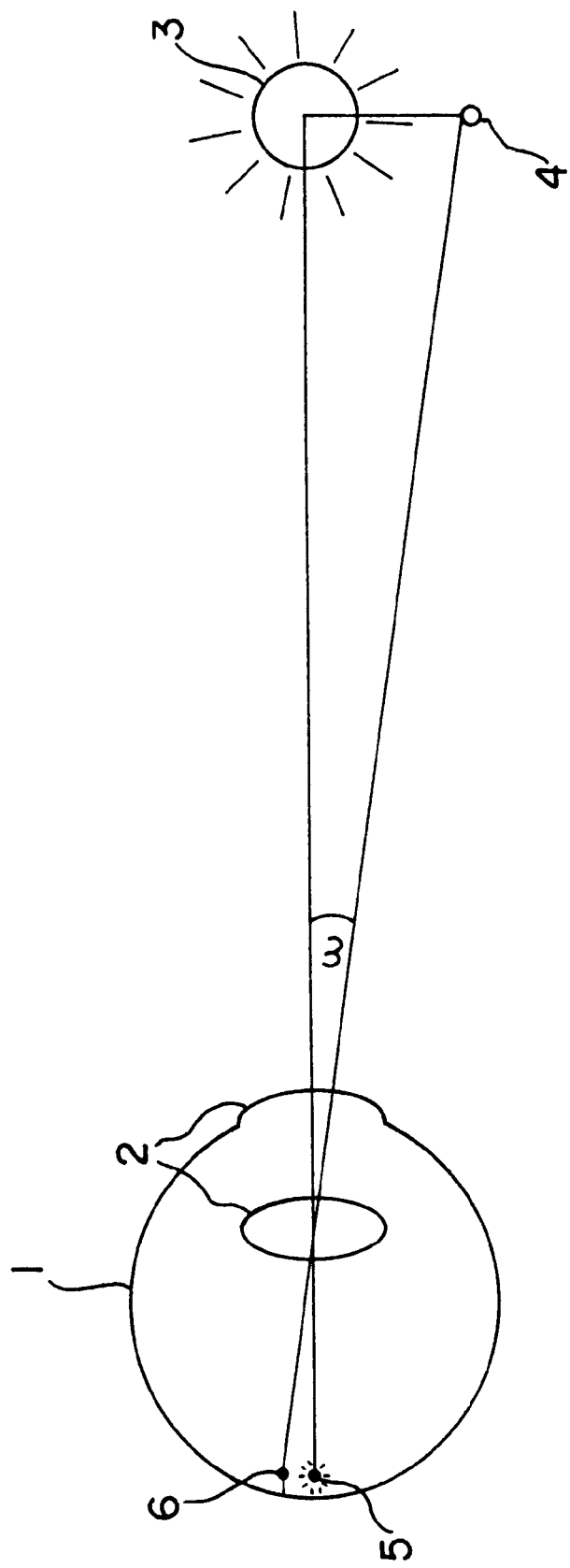

United States Patent

Seguin et al.

Patent Number: 6,007,203
Date of Patent: Dec. 28, 1999

[54] PROCESS OF ASSESSMENT OF OCULAR DYSFUNCTIONS AND IMPLEMENTATION DEVICES OF THIS PROCESS

[75] Inventors: Marie-Christine Seguin, Principality of Monaco, Monaco; Mark A. Babizhayev, Ivanovskaya 20, 74, 127434 Moscow, Russian Federation

[73] Assignees: Exsymol S.A.M., Principality of Monaco, Monaco; Mark A. Babizhayev, Moscow, Russian Federation

[21] Appl. No.: 09/120,311

[22] Filed: Jul. 22, 1998

[30] Foreign Application Priority Data

Jul. 22, 1997 [MC] Monaco ............. 2382

[51] Int. Cl.⁶ ............. A61B 3/10
[52] U.S. Cl. ............. 351/211
[58] Field of Search ............. 351/200, 202, 351/208, 211, 212, 237, 239, 243

[56] References Cited

U.S. PATENT DOCUMENTS

| | | | |
|---|---|---|---|
| 4,917,480 | 4/1990 | Kato et al. | 351/211 |
| 5,042,940 | 8/1991 | Iwamoto | 351/208 |
| 5,223,865 | 6/1993 | Shirao et al. | 351/243 |

FOREIGN PATENT DOCUMENTS

| | | |
|---|---|---|
| 0 002 031 B1 | 5/1979 | European Pat. Off. . |
| 0 002 039 A1 | 5/1979 | European Pat. Off. . |

OTHER PUBLICATIONS

Kafarski et al., "Biological Activity of Aminophosphonic Acids," 63 *Phosphorus, Sulfur, and Silicon* 193–215 (1991).

*Primary Examiner*—George Manuel
*Attorney, Agent, or Firm*—Lydon & Brown, LLP

[57] ABSTRACT

Process of assessment of ocular dysfunctions, characterized in that the patient's eye (1) is placed to a previously defined distance from a lightening glare source (3), so that he can visualize a target (4) placed next to the lightening glare source (3), then the target (4) is approached from the source (3) so that the patient becomes unable to distinguish the target (4) from the source (3) and then, the target (4) is slowly taken away from the source (3), up to the exact moment when the patient distinguishes again the target (4), and at this time, the incident light angle o between the source (3) and the target (4) is measured.

13 Claims, 2 Drawing Sheets

PROCESS OF ASSESSMENT OF OCULAR DYSFUNCTIONS AND IMPLEMENTATION DEVICES OF THIS PROCESS

The invention concerns a new process of assessment of ocular dysfunctions, and the application of this process to measure the ocular media opacities and to control the retinal functions, and implementation devices of this process.

To evaluate the loss or the weakness of some ocular functions that patients with eye troubles complain about, visual acuity is generally measured. This measurement, however, is not always sufficient, notably to answer to the needs of patients with cataract for instance, who complain of troubles due to impairment of contrast and glare sensitivity.

It seems that visual distortion produced by cataract comes from an increase in light scattering, resulting from the opacities in the ocular media. By ocular medium is meant the cornea, the vitreous humour and the lens.

Visual acuity can be measured clinically and contrast sensitivity tests can be realised too. However, these tests do not provide a precise assessment of cataract. They do not allow to predict the results of the cataract's surgery and, particularly, they do not allow to distinguish, in the pathology, between the contribution coming from the retinous degeneration and the one coming from the ocular medium opacities. Finally, contrast sensibility tests of the prior art do not have a reliable reproducibility.

Besides, as visual acuity loss, contrast sensibility loss is not specific of this pathology. Thus, if a patient suffers from cataract and simultaneously from another pathology of visual functions, the clinician cannot know, based on the prior art tests, in which way the contrast sensibility or visual acuity loss results from cataract or from the other pathology.

To notably remedy these drawbacks, one of the aims of the present invention is to propose a new process of ocular dysfunctions assessment that allows notably to diagnose a cataract, to quantify its evolution and the results that come from the administration of anti-cataract medications or foresee the results of a future cataract surgery.

As a matter of fact, the process according to the invention enables measurement of the sight of the eye's central axis and to distinguish, on one hand, the troubles due to opacities in the sight's central axis, and on the other hand the troubles due to the opacities remaining in the rest of the ocular medium.

The process according to the invention is characterized in that the patient's eye is placed to a previously defined distance from a lightening glare source, so that he can visualize a target placed next to the lightening glare source, then the target is approached from the source so that the patient becomes unable to distinguish the target from the source and then, the target is slowly taken away from the source, up to the exact moment when the patient distinguishes again the target, and at this time, the incident light angle between the source and the target is measured.

Preferably, the previously defined distance between the light source and the patient's eye is 300 mm.

Advantageously, the lightening glare source is a halogen lamp or an incandescent lamp.

Preferably, the target is luminous.

According to a special embodiment of the invention, the target is a light scattered source, of red or green colour.

Preferably, the contrast is artificially modified on the target.

According to another special embodiment of the invention, the source and the target are in the same vertical and tangential plan and, in this case, the measurement of the incident light angle between the source and the target is made by measuring the distance between the source and the target.

The process according to the invention is widely applied for the assessment of opacities in ocular media. It is also advantageously used in order to control the retinal functions.

An other aim of the invention is to propose an implementation device of this process, characterized in that it includes, at the height of the patient's eye, a lightening glare source and a target which are possibly able to slide on a ruler.

Preferably, the device according to the invention includes besides a conic tube or a cylindrical tube in order to direct the patient's field of view.

Another aim of the invention is to propose an implementation device of this process, characterized in that it is adapted to an ophthalmologic device for measuring the visual acuity either simply hemispherical, or with an hemispherical perimeter.

Preferably, the ophthalmologic device for measuring the visual acuity with hemispherical perimeter on which is adapted the device according to the invention includes a measuring software.

The description which follows must be read along with both enclosed figures, and non limitatively illustrates the invention.

The FIG. 1 represents in a simplified manner the process according to the invention, ω being the incident light angle between the source and the target.

Figure 2:
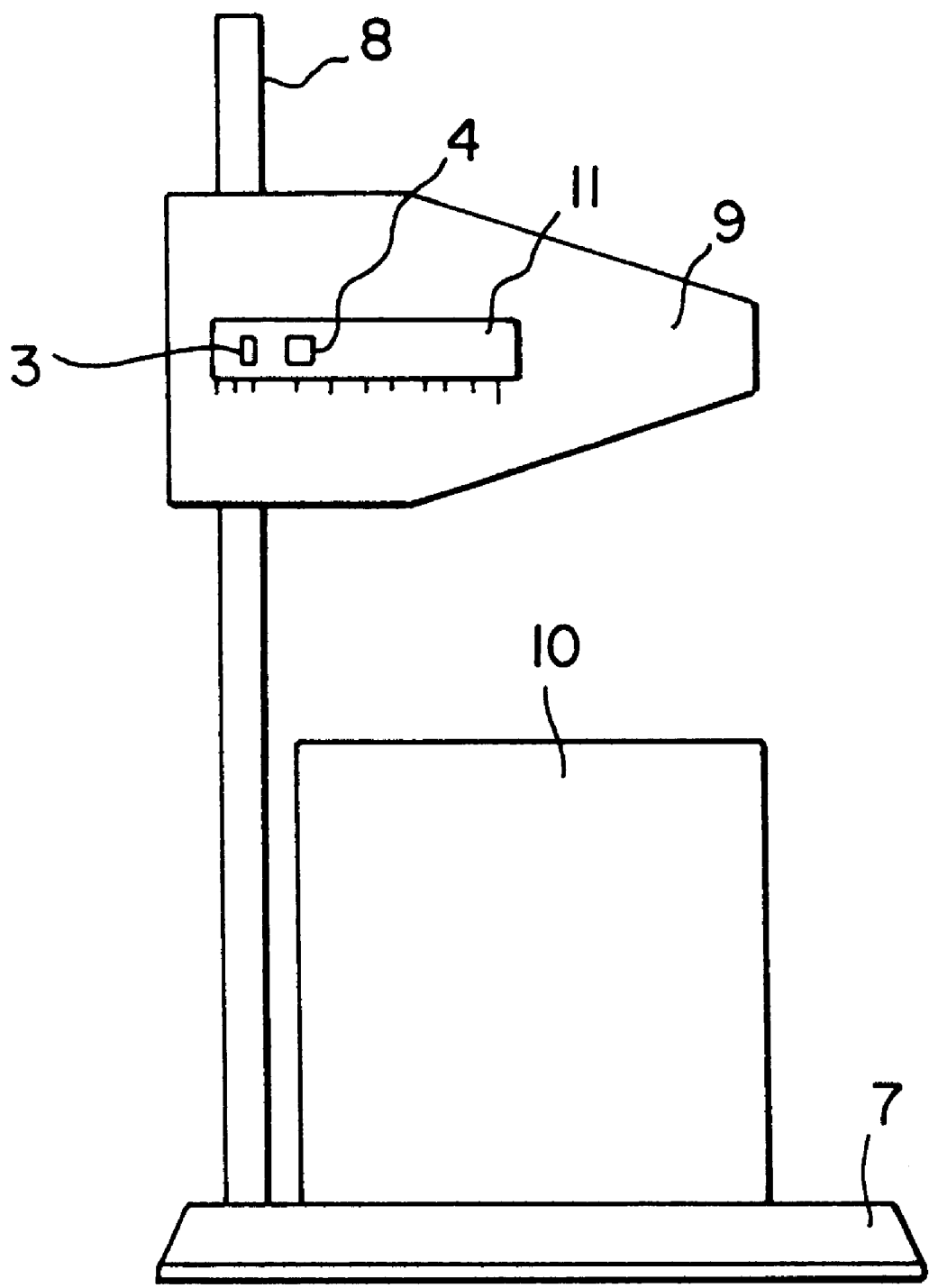

The FIG. 2 represents a simplified front view of a special implementation device of this process according to the invention.

In order to deliver correct information on the cataract's assessment, a test must answer to two criteria: reflect the loss of the visual functions and not be linked to the measurement of the visual acuity.

Patients with cataract often complain about a loss of their ability to see things brightly lighted by the sun light and to be strongly dazzled by the cars' lights arriving in front of them during the night driving.

The process according to the invention is based according to the following observation: as cataract damages the contrasts perceived by the eye 1 of the patient, a way to evaluate it is to modify the contrast on a target 4, preferably luminous, placed next to a lightening glare source 3, and to measure the angle ω of the incident light between the source 3 and the target 4, from the time when the patient can recognize the target 4. This angle ω corresponds to the projection of the source 3 on the eye's retina 1 of the patient.

The a lightening glare source 3 imitates the crossing of the sun light in the ocular medium 2.

The process according to the invention can be carried out according to the following procedure: the patient is placed in a darkened room. If necessary, the patient is subjected to the best visual correction which needs its state (glasses, contact lenses) . Only one of both eyes 1 is examined, and the other eye is hidden with an opaque matte. The patient is placed in front of the device, so that the eye 1 should be to a previously defined distance of a lightening glare source 3, preferably at 300 mm from this source 3.

For the accuracy of the measurement, it is important that the eye 1 of the patient must be in front of the device.

According to a special embodiment of the invention, the device can be equipped with a conic or cylindrical tube, preferably opaque, enabling to restrict the patient's field of view.

According to a special embodiment of the invention the lightening glare source 3 is an halogen lamp or a simple incandescent lamp.

Next to the source 3, but to a sufficient way so that the patient, despite of the glare due to the lightening glare source 3, can see it, the target 4 is fixed. Preferably, the target 4 is luminous. According to a special embodiment of the invention, the target 4 is made with one or several luminous number(s) or sign(s).

According to a preferred embodiment of the invention, the target is made from Landolt rings, which are more especially adapted in order to measure the visual acuity and the contrast sensitivity.

According to a special embodiment of the invention, the target surface is about 5 mm².

The operator approaches the target 4 from the source 3 so that the patient cannot distinguish anymore the target 4 from the source 3. In order to avoid the artefacts due to the retinal persistence, none measurement is made at this time.

Then, slowly, the operator takes away the target 4 from the lightening glare source 3, up to the exact moment when the patient distinguishes again the target 4. This specific moment, is indicated by the patient to the operator and it constitutes the threshold value. The later measures the angle ω of incident light between the source 3 and the target 4.

The index I is the scattered light and answers to the following equation:

$$I = I_0 \cos^2 \omega$$

in which:
$I_0$ is the maximum intensity of light
ω is the incident light angle between the source and the target.

The angle of incident light between the source 3 and the target 4 can be measured in different ways: according to a first embodiment of the invention, the target 4 and the source 3 are in the same vertical plan, tangential according to the emitted light. In this case, in order to measure the angle ω of the incident light between the source 3 and the target 4, it is only necessary to measure its projection (5,6) on this vertical plan, which means to measure the distance between the source 3 and the target 4.

According to an other embodiment of the invention, the target 4 and the lightening glare source 3 are not in the same vertical plan, in this case, the angle ω of the incident light between the source 3 and the target 4 can be measured by any appropriate mean, particularly by an appropriate arithmetic software.

As it is known, the light scattering by ocular mediums 2 depends of the opacity of the crystalline lens, this measurement enables to calculate the scattered light radius and thus the sensivity of the patient to the glare. This measurement can be used, for a series of assessments for the same patient, as a relative index of the transparency of the examined ocular medium 2. This is the reason why the opacities of the vitreous humour can notably be measured.

Another benefit of the process according to the invention is that it enables to measure slight modifications in the opacity of the examined ocular medium 2, which can be noticed by a variation of the threshold value, and to give more details compared to the processes and the devices of the prior art.

According to a special embodiment of the invention, we used as target 4 a light scattered source with a red or green colour, which enables the assessment of the wave-length of the scattered light. Preferably, the green light scattered source flux is 0,75 lux, the red light scattered source flux is 1,7 and the glare light scattered source flux is 1000 lux; the ratio between the glare light scattered source flux on the green source is around 1333; the ratio of the glare light scattered source flux on the red source is around 588.

If a conic or cylindrical tube is used in order to direct the sight field of the patient, it is possible to use far smaller values for the light scattered flux.

Advantageously, the different sources of lights are equipped with means enabling to vary their scattered flux.

The preferred values for the scattered flux can possibly vary according to the use of a device in accordance with the invention, and more especially with its possible adaptation on a device with hemispheric perimeter.

The process according to the invention can be the object of the implementation of a specific device in which the source 3 and the target 4 are situated on the ruler 11, on which they slide, the light scattered source 3 can be placed on the right or on the left of the target 4. Preferably, the ruler is horizontal.

Preferably, the device according to the invention includes a base 7, on which is fixed the extremity of a vertical rod 8 which carries a mobile case 9 along the rod 8. The case 9 supports an horizontal rule 11 on which can slide the target 4 and/or the lightening glare source 3.

The lightening glare source 3 and the target 4 are supplied with an electric source supply 10.

According to an embodiment of the invention, the process according to the invention can be adapted on an equipment with hemispheric perimeter which is usually used in order to measure the visual acuity. This type of equipment is already commonly used by the ophthalmologists for their daily clinical tests.

According to an other embodiment of the invention, the process according to the invention can be adapted on an hemispheric equipment type "B.A.T." (Brightness Acuity Tester) commercialized by the American company MENTOR O&O Inc. The B.A.T. has an hemispheric lightening glare source: e.g. an hemispheric bowl with a diameter of 60 mm with a(n) (central) opening of 12 mm, from which the patient puts his/her eye. The patient will be able to distinguish numerous light scattered sources, which appear at various points of the hemisphere.

It must be underlined that the B.A.T. is not a device with perimeter, and this is the reason why it can be used in order to measure the vision of the central axis of the patient's eye but not to measure the peripheral vision.

However, a drawback of the B.A.T. (Mentor O&O Inc.) is that the glare source appears on the whole hemisphere which diminishes the eye's sensitivity to contrast.

According to a preferred embodiment of the invention, the glare source is punctual (and not hemispheric) and in the central axis of the patient's vision, it enables to evaluate the only contribution of the opacified area in the ocular medium which decreases the contrast.

According to a special embodiment of the invention, at least one of the light scattered source can be emitted and controlled by a computer. Preferably, the concerned light scattered source will be the target because the usual scattering intensity emitted by the computers is too weak to create the necessary glare to the glare source. The lightening glare source is thus advantageously separated from the computer.

However, a reflection device for an external source by a mirror, controlled by a computer can be advantageously set up: this embodiment has the advantage to enable the operator to control with the computer the lightening glare source flux reflected by the mirror and the lightening flux of the target.

The use of a computer is particularly adapted in order to test the central vision and the effects of glare as the computers displays which are usually used by the person skilled in the art are opened to an angle of 15–25°.

The standardization of the devices according to the invention can be made using aqueous suspensions of latex particles. Preferably, the latex particles have a diameter of 1,5 μm. Optical density is measured on each latex suspension by spectrophotometry (in vitro). Then a volunteer, who is not attacked, is installed in front of the device according to the invention, and each suspension of latex is successively placed in front of his eye. ω is measured and the relation between the optical density of the suspension (which imitates the lens opacity of the attacked patient, to various steps) and ω is recorded.

We claim:

1. A process for assessment of ocular dysfunction in a patient, comprising placing a patient's eye at a previously defined distance from a glare light source, such that the patient can visualize a target placed next to the glare light source;

moving said target closer to said glare light source until said patient is unable to distinguish said target from said glare light source; and moving said target away from said glare light source up to the exact moment when the patient distinguishes again said target, and measuring at that moment an incident light angle between said glare light source and said target.

2. The process of claim 1, wherein the patient is first placed in a darkened room.

3. The process of claim 1, wherein said previously defined distance between the glare light source and the patient's eye is 300 mm.

4. A device for assessment of ocular dysfunction in a patient, comprising a glare light source;

a target adapted to be placed next to said glare light source;

means for moving said target towards and away from said glare light source;

means for measuring an incident light angle between the glare light source and said target.

5. The device of claim 4, wherein said glare light source is a halogen lamp or an incandescent lamp.

6. The device of claim 4, wherein said target is luminous.

7. The device of claim 6, wherein said target is a light scattered source of red or green color.

8. The device of claim 4, wherein said glare light source and said target are in the same vertical and tangential plane.

9. The device of claim 8, wherein said incident light angle between said glare light source and said target is measured by measuring the distance between said glare light source and said target.

10. The device of claim 4, wherein said means for moving said target towards and away from said glare light source comprises a ruler upon which said target and said glare light source are slidably mounted.

11. The device of claim 4, further comprising a conic tube or a cylindrical tube adapted to direct the patient's sight field.

12. The device of claim 4, in combination with an opthalmologic device for measuring the visual activity of a patient and having a hemispheric glare light source.

13. The device of claim 12, wherein said ophthalmologic device includes a measuring software.

* * * * *